(12) United States Patent
Owoo et al.

(10) Patent No.: US 7,915,290 B2
(45) Date of Patent: *Mar. 29, 2011

(54) ARGATROBAN FORMULATIONS AND METHODS FOR MAKING AND USING SAME

(75) Inventors: George Owoo, North Plainfield, NJ (US); Richard A. Burgos, Rahway, NJ (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 48 days.

This patent is subject to a terminal disclaimer.

(21) Appl. No.: 12/040,756

(22) Filed: Feb. 29, 2008

(65) Prior Publication Data

US 2009/0221636 A1 Sep. 3, 2009

(51) Int. Cl.
*A61K 31/47* (2006.01)
(52) U.S. Cl. .................................. 514/312
(58) Field of Classification Search ............ 514/312
See application file for complete search history.

(56) References Cited

U.S. PATENT DOCUMENTS

| | | | |
|---|---|---|---|
| 4,227,006 A | 10/1980 | Okamoto et al. | |
| 5,214,052 A | 5/1993 | Ofuchi et al. | |
| 5,506,241 A * | 4/1996 | Mano et al. | 514/317 |
| 5,565,471 A * | 10/1996 | Ozaki | 514/312 |
| 5,605,892 A * | 2/1997 | Ikejiri et al. | 514/58 |
| 5,679,690 A * | 10/1997 | Andre et al. | 514/314 |
| 5,849,843 A | 12/1998 | Laurin | |
| 5,998,019 A | 12/1999 | Rosenbaum | |
| 6,087,375 A | 7/2000 | Bridon | |
| 7,589,106 B2 * | 9/2009 | Palepu | 514/314 |
| 2007/0049617 A1 | 3/2007 | Owoo et al. | |

FOREIGN PATENT DOCUMENTS

| | | |
|---|---|---|
| EP | 0008746 | 3/1980 |
| EP | 0301970 | 2/1989 |
| EP | 0565897 | 10/1993 |
| EP | 0608828 | 8/1994 |
| EP | 0608831 | 8/1994 |
| EP | 0621036 | 10/1994 |
| EP | 0669131 | 8/1995 |
| JP | 1031656 | 2/1989 |
| WO | WO 0067772 A1 * | 11/2000 |
| WO | 2005009361 | 2/2005 |
| WO | 2005009371 | 2/2005 |
| WO | 2007027565 | 3/2007 |

OTHER PUBLICATIONS

GSKARL3-Search performed for acetic acid dissolve argatroban, [online], [retrieved on Aug. 18, 2008], Retrieved from the internet;,URL:http://us.gsk.com/products/assets/us-argatroban.pdf>.*
Remington—The sciences and Practice of Pharmacy, 20th edition, 2000.*
Argatroban—Wikipedia, the free encyclopedia; http://en.wikipedia.org/wiki/Argatroban dated May 16, 2007 (2 pgs.).
Mechanism of Action; Anticoagulant Therapy—Argatroban Mechanism of Action; http://www.argatroban.com/argatroban_mechanism.htm dated May 16, 2007 (1 pg.).
Dosage & Administration; Argatroban Dosage & Administration; http://www.argatroban.com/argatroban_dosage.htm dated May 16, 2007 (3 pgs.).
Written Opinion of the International Searching Authority (6 pgs.).

* cited by examiner

*Primary Examiner* — Raymond J Henley, III
(74) *Attorney, Agent, or Firm* — K&L Gates LLP

(57) ABSTRACT

Formulations comprising argatroban and methods of making and using the formulations are provided. In an embodiment, the formulation comprises a solution having an argatroban concentration ranging from greater than about 10 to about 500 mg/mL. The solution can comprise an aqueous solution. The solution can be packaged in a sealed container that may either be aseptically-filled or subjected to sterilization to reduce the microbiological burden of the formulation. The solution can further be diluted and administered to persons needing same.

9 Claims, No Drawings

ARGATROBAN FORMULATIONS AND METHODS FOR MAKING AND USING SAME

BACKGROUND

The present disclosure relates to new formulations of 1-[5-[(aminoiminomethyl)amino]-1-oxo-2-[[(1,2,3,4-tetrahydro-3-methyl-8-quinolinyl) sulfonyl]amino]pentyl]-4-methyl-2-piperidinecarboxylic acid hydrate, commonly known by the generic name "argatroban." Argatroban is a synthetic direct thrombin inhibitor derived from L-arginine and is a useful anti-coagulant and anti-thrombotic agent.

Argatroban is considered slightly to very slightly soluble in water according to the USP classification of solutes, with solubility on the order of 0.8 to 0.9 mg/mL. It is also both light and heat-sensitive and tends to degrade unless stabilized. Argatroban is commercially available in concentrated form in an aseptically-filled vial containing, per mL, 100 mg argatroban, 750 mg D-sorbitol and 1000 mg dehydrated alcohol.

SUMMARY

Formulations comprising argatroban and methods of making and using the formulations are provided. In a general embodiment, the present disclosure provides a solution comprising argatroban dissolved in an acid. For example, the solution can have an argatroban concentration ranging from greater than 10 mg/mL to about 500 mg/mL. The solution may optionally further contain a buffering agent to help maintain pH and an osmotic-adjusting agent to enhance infusion properties. The solution is storage-stable (both light and heat), capable of being aseptically-filled and sterilized (e.g. heat), and contains argatroban in a range of concentrations, which can be diluted prior to administration. The solution can have an extended shelf life.

In an embodiment, the argatroban concentration ranges from about 15 mg/mL to about 250 mg/mL. The solution can also have a pH ranging from about 2.3 to about 8.5. The pH can be lowered using suitable acid such as, for example, phosphoric acid, acetic acid, tartaric acid, citric acid, formic acid, malic acid, hydrochloric acid and combinations thereof.

In an embodiment, the solution can further comprise a first solvent such as, for example, propylene glycol, polyethylene glycol 100-400, benzyl alcohol and combinations thereof. The solution can also comprise a mixture of two or more solvents.

In an embodiment, the solution can comprise a buffering agent such as, for example, acetate, glutamate, citrate, tartrate, benzoate, lactate, malate, gluconate, phosphate, glycine and combinations thereof. The buffering agent can also be a corresponding salt of the acid. The solution can also comprise an osmotic agent selected from the group consisting of sodium chloride, calcium chloride, potassium chloride, dextrose, sodium lactate and combinations thereof.

In another embodiment, the present disclosure provides a solution comprising argatroban dissolved in a first solvent and a second solvent. The solution has an argatroban concentration ranging from about 1 mg/mL to about 500 mg/mL. Preferably, the argatroban concentration ranges from greater than 10 mg/mL to about 250 mg/mL. The first solvent and second solvent can be, for example, propylene glycol, polyethylene glycol 100-400, benzyl alcohol and combinations thereof. The solution can further comprise an acid.

In a further embodiment, the present disclosure provides a method for preparing formulations comprising argatroban in a sealed container, such as an ampoule, vial, syringe or infusion bag, and autoclaving for a period of time sufficient to render the formulation sterile.

In another embodiment, the present disclosure provides a method for producing a medical product. The method comprises providing a solution having an argatroban concentration ranging from greater than 10 mg/mL to about 500 mg/mL and applying the solution to a surface of a medical device. The medical product can be, for example, a transdermal patch, a stent, a polymeric substrate and combinations thereof. The method can further comprise drying the solution and forming a coating of argatroban on the medical device.

In yet another embodiment, the present disclosure provides a method of providing anticoagulation and/or antithrombotic therapy to a person. The method comprises administering to a person in need of anticoagulation and/or antithrombotic therapy a solution comprising argatroban dissolved in an acid and/or one or more solvents. The solution has an argatroban concentration greater than 10 mg/mL to about 500 mg/mL.

An advantage of the present disclosure is to provide improved formulations comprising argatroban.

Another advantage of the present disclosure is to provide sterilized solutions comprising argatroban.

Yet another advantage of the present disclosure is to provide stable solutions comprising argatroban.

Still another advantage of the present disclosure is to provide improved methods of making formulations comprising argatroban.

Another advantage of the present disclosure is to provide ready to use solutions comprising a sterilized and stable amount of argatroban.

Additional features and advantages are described herein, and will be apparent from, the following Detailed Description.

DETAILED DESCRIPTION

The present disclosure relates to solutions comprising argatroban having enhanced solubility and methods of making and using the argatroban solutions. In a general embodiment, the solution has an argatroban concentration ranging from greater than about 10 to about 500 mg/mL. The solution can be an aqueous solution. In an embodiment, the solutions can be packaged in a sealed container that may either be aseptically-filled or subjected to terminal sterilization to reduce the microbiological burden of the formulation. The present solutions can be stable against hydrolytic degradation and other adverse chemical reactions, and when packaged appropriately, for example, with amber containers, non-light transmitting polymer containers or aluminum overpouches, can be stable against photolytic degradation.

It has been surprisingly found that higher concentrations (>10 mg/L) of argatroban can be solubilized and stabilized in solutions using added dilute acids and/or solvents. Furthermore, combinations with other co-solvents in embodiments of the present disclosure can provide improved stability of the formulations. The solutions comprising argatroban in embodiments of the present disclosure can possess a better dissolution profile when diluted prior to the administration to patients than conventional techniques, for example, due to the increased solubility of the argatroban.

In an embodiment, the present disclosure provides a solution comprising argatroban dissolved in a dilute acid. For example, the solution comprises an argatroban concentration ranging from greater than 10 mg/mL to about 500 mg/mL or any value therebetween. The argatroban concentration may be varied based on the type and concentration of the acid. The argatroban concentration of the solution may range from about 15 mg/mL to about 500 mg/mL, or from about 5 mg/mL to about 250 mg/mL, or from about 20 mg/mL to about 200 mg/mL, or from about 50 mg/mL to about 150 mg/mL. In a further embodiment, the argatroban concentration of the solution ranges from about 100 mg/mL, or 100 mg/mL. The solution may be free of dehydrated alcohol and D-sorbitol.

Nonlimiting examples of suitable acids for dissolving the argatroban include phosphoric acid, acetic acid, tartaric acid, citric acid, formic acid, malic acid, hydrochloric acid and combinations thereof. The acids can be typically employed in the solution at concentrations ranging from 0.01 to 3 N, depending on the degree of ionization and association of the counter-ion stability in an aqueous environment. The preferred acid is acetic acid, and will be present in an amount ranging from 0.05 to 6 mg/mL. In an embodiment, the acetic acid is glacial acetic acid having a normality from about 2N to about 10N. In an alternative embodiment, the pH of the dilute acid solution may be from about 1.0 to about 3.5 or any value therebetween.

In an alternative embodiment, the argatroban solution comprising argatroban dissolved in one or more solvents in addition to the acid. It has been unexpectedly found that one or more solvents in combination with the dilute acid provides an argatroban solution with improved stability and a longer shelf life. Not wishing to be bound by any particular theory, it is believed that the solvent(s)/acid combination improves stability and shelf life by stabilizing the pH of the solution and/or maintaining the solubility of the in-situ salt over greater time durations. The solvent provides stability and dissolution of the dissolved argatroban from about pH 2.3 to about pH 8.5. The argatroban solution is stable and has an extended shelf life (e.g. greater than about three weeks). In an embodiment, the argatroban solution has a shelf life from about at least three weeks to about two months. In an alternative embodiment, the argatroban solution includes one or more solvents with no added acid.

Nonlimiting examples of suitable solvents include propylene glycol, a polyethylene glycol having a molecular weight from about 100 to about 1000 or any molecular weight therebetween, benzyl alcohol and combinations thereof. In an embodiment, the polyethylene glycol has a molecular weight from about 200 to about 400.

In another embodiment, the solution utilizes a co-solvent (i.e., at least two solvents) matrix to dissolve the argatroban. For example, the solution can include argatroban dissolved in a first solvent that is propylene glycol or polyethylene glycol and a second solvent. The solution can have an argatroban concentration from about 1 mg/mL to about 500 mg/mL. Preferably, the argatroban concentration ranges from greater than 10 mg/mL to about 500 mg/mL. The second solvent may be a propylene glycol or polyethylene glycol that is different than the first or benzyl alcohol. In a further embodiment, the first solvent may be a polyethylene glycol having a first molecular weight and the second solvent may be a polyethylene glycol having a molecular weight different than the molecular weight of the first polyethylene glycol. The solution may also include an acid as previously disclosed herein.

In yet another embodiment, an acid, a base or a buffering agent may be added to the solution to maintain the pH from about pH 2.3 to about pH 8.5 or from about pH 4.5 to about pH 6.5. Nonlimiting examples of suitable buffering agents include acetate, glutamate, citrate, tartrate, benzoate, lactate, malate, gluconate, phosphate, glycine and combinations thereof. In an embodiment, the buffering agent may be a salt of the acid. For example, the acid may be acetic acid and the buffering agent may be sodium acetate. Other nonlimiting acid-buffering agent combinations include tartaric acid-sodium tartrate, citric acid-sodium citrate, formic acid-sodium formate, malic acid-sodium malate, hydrochloric acid-sodium chloride, benzoic acid-sodium benzoate, glutamic acid-sodium glutamate, lactic acid-sodium lactate, gluconic acid-sodium gluconate, phosphoric acid-sodium phosphate and combinations thereof. It is understood that any of the foregoing buffering agents may include an alkali metal or an alkaline earth metal.

The argatroban solutions of the present disclosure can be diluted to a desired concentration, for example, prior to dosing patients in need of anticoagulation therapy via suitable parenteral routes of administration. In an embodiment, a suitable pharmaceutically acceptable acid can be added to control the solubility and stability of the solution. Suitable osmotic-adjusting agents known in the art can be added to various formations of the solutions in an amount ranging from about 1 to about 500 mg/mL.

The argatroban solutions of the present disclosure can be packaged in a sealed container and be rendered sterile by aseptic processes or suitable sterilization techniques (e.g. heat). The argatroban solutions can also be packaged in any suitable containers known in the art such as, for example, vials, syringes, bags, bottles and ampoules. The containers can be fabricated from glass or from any other suitable polymeric materials. Ready-to-use formulations are typically packaged in vials, syringes, infusion bags and bottles, while concentrated formulations are typically packaged in ampoules.

As previously discussed, the enhanced solubility of argatroban in aqueous solution can be accomplished by the addition of one or more acids. The acids can typically be dilute, meaning on the order of 0.01 to 3 N. Though not wishing to be limited to any one theory, it is believed that the acid (which may be either organic or inorganic) forms an "ionic liquid" or in-situ salt solution of argatroban. This refers to an ionic liquid and counter ion of salt where the ions are poorly or randomly arranged and/or coordinated.

Table 1 provides a summary of enhanced solubility of argatroban in dilute acids.

TABLE 1

Solubility of Argatroban in dilute acids at room temperature

| Dilute acids[1] | Visual Dissolution[2] | Amount (mg/mL)[3] |
|---|---|---|
| Phosphoric acid | Freely soluble | ≥10.08 |
| Acetic acid | Very soluble | ≥11.5 |
| Tartaric acid | Freely soluble | ≥10.4 |
| Citric acid | Moderately soluble | ≥9.79 |
| Formic acid | Very soluble | ≥10.08 |
| Maleic acid | Moderately soluble | ≥9.32 |
| Hydrochloric acid | Moderately soluble | ≥10.1 |

[1]The molarity of the acids used were ~1-3 N
[2]Classification according to Remington's Pharmaceutical Science, 20$^{th}$ edition
[3]Amount of argatroban was determined by HPLC method In the present specification, the term "stable" means remaining in a state or condition that is suitable for administration to a patient. Formulations according to embodiments of the present disclosure are found to be stable when maintained at room temperature for at least 24 months, and are generally stable at room temperature for 24 to 36 months.

In the present specification, the term "sterile" composition or solution means a composition or solution that has been brought to a state of sterility and has not been subsequently exposed to microbiological contamination (e.g. the container holding the sterile composition or solutions has not been compromised). Sterile compositions or solutions are generally prepared by pharmaceutical manufacturers in accordance with current Good Manufacturing Practice ("cGMP") regulations of the U.S. Food and Drug Administration.

The argatroban solutions in an embodiment of the present disclosure can take the form of a sterile, stable, ready-to-use formulation for infusion. For example, this can avoid the inconvenience of diluting a concentrated argatroban small volume parenteral formulation into infusion diluents prior to infusion, as well as eliminate the risk of microbiological contamination during aseptic handling and any potential calculation or dilution error. Such formulations, not being prepared from a concentrate, may be essentially free from saccharide component, e.g. D-sorbitol, and dehydrated alcohol component, e.g. dehydrated ethanol. Nevertheless, the argatroban solutions in alternative embodiments can also take the form of a concentrated formulation that can be diluted prior to administration.

The aqueous, sterile, stable solutions in embodiments of the present disclosure can be suitable for parenteral administration to a patient. For example, the solution may be administered in the form of a bolus injection or intravenous infusion. Suitable routes for parenteral administration include intravenous, subcutaneous, intradermal, intramuscular, intraarticular, and intrathecal. The ready-to-use formulation of the disclosure can be administered by intravenous infusion.

No buffering agent may necessary when the argatroban formulations of the present disclosure are stored in certain types of containers because the argatroban formulation can be inherently stable. Suitable such containers are those whose surfaces in contact with the argatroban formulation do not contain leachable substances, which are typically alkaline. One such suitable container is Baxter Healthcare Corporation's IntraVia® flexible plastic container. The pHs of the solutions in the case where no buffering agent is used will generally range from about 4.5 to 5.5.

If used, suitable physiologically-acceptable buffering agents can include acetate, glutamate, citrate, tartrate, benzoate, lactate, malate, gluconate, phosphate and glycine, with acetate being preferred. A preferred buffering system comprises a combination of sodium acetate and acetic acid. Buffering agents can be present in the solution in a concentration that depends from the concentration of argatroban. The concentration will typically range from 0.05 to 200 mM and from 10 to 100 mM for formulations containing 0.5 to 10 mg/mL argatroban.

Suitable diluent containing osmotic-adjusting agents, when used, can be compatible with the pH requirements of the present formulation, and include one or more of sodium chloride, reduced sugars, calcium chloride, potassium chloride, dextrose and sodium lactate. Preferred are sodium chloride and dextrose that provide an iso-osmotic solution for infusion. In alternative embodiments, the formulations of the present disclosure may contain 0 to 100 mg/mL osmotic-adjusting agent; preferably 14 to 60 mg/mL sodium chloride, more preferably 14 to 10 mg/mL sodium chloride; or dextrose in an amount up to 5% (weight by weight), typically in an amount ranging from 25 to 60 mg/mL. In a further embodiment, the buffering agent and the osmotic agent may be the same composition.

Argatroban solutions according to the present disclosure can be prepared into small volume parenteral (SVP) and large volume parenteral (LVP) dosage forms. The dosage forms can be held in any suitable container. Suitable containers include, for example, glass or polymeric vials, ampoules, syringes or infusion bags with sizes ranging from 1 ml to 500 ml. SVP ready-to-use solutions are typically filled into ampules and vials in 1 to 100 mL presentations. In addition, syringes can be used as the container for a ready-to-use SVP, which are sold as "pre-filled syringes". The LVP presentations can be contained in infusion bags or bottles.

Polymeric containers are preferably flexible and can contain or be free of polyvinylchloride (PVC). It should be appreciated that all types of polymer materials for pharmaceutical and medical products (e.g. PVC, polypropylene, etc.) can be used for the polymeric containers. For premixed solutions at higher concentrations, preferred containers are free of PVC, such as those disclosed in U.S. Pat. Nos. 5,849,843 and 5,998,019, the entire disclosures of which are herein incorporated by reference. Polymeric containers can further be provided with a moisture barrier as a secondary packaging system to prevent the loss of water during storage and to further ensure the stability of the formulation (e.g. when terminal sterilization is involved). A preferred moisture barrier is an aluminum overpouch, which will also protect the formulation from photolytic degradation.

Procedures for filling formulations of the present disclosure in containers and their subsequent processing are known in the art. These procedures are used to produce sterile pharmaceutical drug products often required for health care. Such processing techniques preferably use a sterilization process to destroy or eliminate any microorganisms that may be present in the argatroban formulations following preparation. For example, terminal heat sterilization can be used to destroy all viable microorganisms within the final, sealed container of the argatroban formulation. An autoclave is commonly used to accomplish terminal heat-sterilization of drug products in their final packaging.

Typical autoclave cycles in the pharmaceutical industry to achieve terminal sterilization of the final product are 121° C. for 15 minutes. The argatroban solution of the present disclosure can be autoclaved at a temperature ranging from 115 to 130° C. for a period of time ranging from 5 to 40 minutes with acceptable stability. Autoclaving is preferably carried out in the temperature range of 119 to 122° C. for a period of time ranging from 10 to 36 minutes.

Alternatively, sterile solutions according to the present disclosure may be prepared using aseptic processing techniques. Aseptic filling is ordinarily used to prepare drug products that will not withstand heat sterilization, but in which all of the ingredients are sterile. Sterility is maintained by using sterile materials and a controlled working environment. All containers and apparatus are sterilized, preferably by heat sterilization, prior to filling. The container (e.g., vial, ampoule, infusion bag, bottle, or syringe) are then filled under aseptic conditions.

In an alternative embodiment, the present disclosure provides a method for producing a medical product. The method includes providing a solution having an argatroban concentration ranging from greater than 10 mg/mL to about 500 mg/mL; and applying the solution to a surface of a medical device. The medical device may be any device capable of delivering argatroban to a patient. Nonlimiting examples of suitable medical products include a transdermal patch, a stent, a polymeric substrate, and any combination thereof.

Application of the solution on the medical device may be by way of spraying the solution onto one or more surfaces of the medical device. Alternatively, the medical device may be immersed in to solution. In an alternative embodiment, the method includes drying the applied solution and forming a coating of argatroban on the medical device.

EXAMPLES

By way of example and not limitation, the following examples are illustrative of various embodiments of the present disclosure.

Example 1

Preparation of a Concentrate Aqueous Pharmaceutical Formulation Comprising Argatroban

| | |
|---|---|
| Argatroban | 100 mg |
| Glacial Acetic Acid, USP | 0.172 mL |
| Water for Injection, USP | q.s. to 1 mL |

The equipment and glassware for compounding, filtering, and filling are properly washed and depyrogenated. The filter assembly, filling tube assembly, and other parts and equipment are sterilized. Eighty percent (80%) of the final volume of cool Water for Injection is collected in a calibrated compounding tank. Acetic acidic is added to the tank and the solution is stirred until completely dissolved. Argatroban is added in the final step and tank is adjusted to 100% of the final volume with Water for Injection. The solution is stirred until complete dissolution is visually verified. This solution is filtered and aseptically filled into glass vials. The filled vials are closed with the stoppers and then sealed with aluminum seals.

The vial units prepared by a similar method as described above were placed on stability test. At each stability point, the samples were tested for pH and concentration of the drug (Assay). The assay was determined by a high performance liquid chromatographic (HPLC) method. The results of this stability testing are summarized in Table 2.

TABLE 2

| Storage Condition | Time Interval | pH | Assay (% Initial) |
|---|---|---|---|
| Ambient | Initial | ND** | 100.0% |
| 5° C. | 3 Weeks | 2.8 | 101.9% |
| | 4 Weeks | 2.8 | 102.0% |
| | 2 Months | 3.0 | 101.9% |
| 25° C./60% RH* | 3 Weeks | 3.0 | 101.3% |
| | 4 Weeks | 3.1 | 102.2% |
| | 2 Months | 3.1 | 101.7% |
| 40° C./75% RH* | 3 Weeks | 3.2 | 101.3% |
| | 4 Weeks | 3.3 | 100.7% |
| | 2 Months | 3.2 | 96.7% |

*Relative Humidity;
**Not Determined

Example 2

Preparation of a Concentrate Aqueous Pharmaceutical Formulation Comprising Argatroban and Mixed Co-Solvents

| | |
|---|---|
| Argatroban | 100 mg |
| Glacial Acetic Acid, USP | 0.1 mL |
| Sodium Acetate, (0.02M) | 0.1 mL |
| PEG 400 (Poly Ethylene Glycol) | 0.2 mL |
| PG (Propylene Glycol) | 0.1 mL |
| Water for Injection, USP | q.s. to 1 mL |

The equipment and glassware for compounding, filtering, and filling are properly washed and depyrogenated. The filter assembly, filling tube assembly, and other parts and equipment are sterilized. Argatroban and Glacial Acetic acid is added to the tank and the solution is stirred until completely dissolved. Sodium acetate, PEG 400 and PG is added in the final step and tank is adjusted to 100% of the final volume with Water for Injection. The solution is stirred until complete dissolution is visually verified. This solution is filtered and aseptically filled into glass vials. The filled vials are closed with the stoppers and then sealed with aluminum seals.

The vial units by a similar method as described above were placed on stability test. At each stability point, the samples were tested for concentration of the drug (Assay). The assay was determined by a high performance liquid chromatographic (HPLC) method. The results of this stability testing are summarized Table 3.

TABLE 3

| Storage Condition | Time Interval | Assay (% Initial) |
|---|---|---|
| Ambient | Initial | 100.0% |
| 25° C./60% RH* | 2 Weeks | 100.0% |
| | 4 Weeks | 99.7% |
| | 6 Weeks | 99.7% |
| | 8 Weeks | 99.6% |
| 40° C./75% RH* | 2 Weeks | 100.1% |
| | 4 Weeks | 100.9% |
| | 6 Weeks | 102.5% |
| | 8 Weeks | 99.6% |

*Relative Humidity

Example 3

| | |
|---|---|
| Argatroban | 10-250 mg |
| Sodium Acetate Trihydrate, USP | 2.8 mg |
| Glacial Acetic Acid, USP | 0.546 mg |
| Polyethylene glycol 400 | 5-30% v/v |
| HCl or NaOH | To adjust pH as required |
| Water for Injection, USP | q.s. |

Example 4

| | |
|---|---|
| Argatroban | 10-250 mg |
| Sodium Acetate Trihydrate, USP | 2.8 mg |
| Glacial Acetic Acid, USP | 0.546 mg |
| Polyethylene glycol 400 | 5-20% v/v |
| Propylene glycol | 5-30% v/v |
| HCl or NaOH | To adjust pH as required |
| Water for Injection, USP | q.s. |

Example 5

| | |
|---|---|
| Argatroban | 10-250 mg |
| Sodium Acetate Trihydrate, USp | 2.8 mg |
| Glacial Acetic Acid, USP | 0.546 mg |
| Polyethylene glycol 400 | 5-20% v/v |
| Benzyl alcohol | 0.5-4% v/v |
| HCl or NaOH | To adjust pH as required |
| Water for Injection, USP | q.s. |

The solutions as described in Examples 3-5 can be diluted to desired concentration prior to dosing patients via suitable parenteral route of administration. The solutions can be sterilized prior to use. The solutions can contain argatroban in an amount ranging from 1-1000 mg/mL, preferably 1-100 mg/mL. Pharmaceutically acceptable acids and solvents can be utilized to control the solubility and stability of the formulation. Suitable osmotic-adjusting agents may be added as known in the art ranging from 1-250 mg/mL. The solutions of the present disclosure can be packaged in sealed containers and made sterile either by aseptic process or terminal sterilization.

The equipment and glassware for compounding, filtering and filling are properly washed and depyrogenated. The filter assembly, filling tube assembly, and other parts and equipment are sterilized. Eighty percent (80%) of the final volume of cool Water for Injection is collected in a calibrated compounding tank. Acetic acid (suitable organic or inorganic acid) is added to the tank, and the solution is stirred until completely dissolved. Argatroban is added in the final step, and the tank is adjusted to 100% of the final volume with Water for Injection. The solution is stirred until complete dissolution is visually verified. This solution is filtered and aseptically filled into glass vials. The filled vials are closed with the stoppers and then sealed with aluminum seals.

Example 6

Preparation of a Concentrate Aqueous Pharmaceutical Formulation Comprising Argatroban

| | |
|---|---|
| Argatroban | 100 mg |
| Acetic Acid, NF (36%) | 0.5 mL |
| Water for Injection, USP | q.s. to 1 mL |

The equipment and glassware for compounding, filtering, and filling are properly washed and depyrogenated. The filter assembly, filling tube assembly, and other parts and equipment are sterilized. Eighty percent (80%) of the final volume of cool Water for Injection is collected in a calibrated compounding tank. Acetic acidic is added to the tank and the solution is stirred until completely dissolved. Argatroban is added in the final step and tank is adjusted to 100% of the final volume with Water for Injection. The solution is stirred until complete dissolution is visually verified. This solution is filtered and aseptically filled into glass vials. The filled vials are closed with the stoppers and then sealed with aluminum seals.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A stable, sterilized, infusion solution comprising argatroban dissolved in an acid, a first solvent selected from the group consisting of propylene glycol, polyethylene glycol 100-1000, benzyl alcohol and combinations thereof, and a second solvent different than the first solvent, the second solvent selected from the group consisting of propylene glycol, polyethylene glycol 100-1000, benzyl alcohol and combinations thereof, the solution having an argatroban concentration ranging from about 15 mg/mL to about 250 mg/mL and a pH ranging from about 4.5 to about 6.5, wherein the acid is selected from the group consisting of phosphoric acid, acetic acid, tartaric acid, citric acid, formic acid, malic acid, hydrochloric acid and combinations thereof.

2. The solution of claim 1 comprising a buffering agent selected from the group consisting of acetate, glutamate, citrate, tartrate, benzoate, lactate, malate, gluconate, phosphate, glycine and combinations thereof.

3. The solution of claim 1 comprising a buffering agent that is a corresponding salt of the acid.

4. The solution of claim 1 comprising an osmotic agent selected from the group consisting of sodium chloride, calcium chloride, potassium chloride, dextrose, sodium lactate and combinations thereof.

5. The solution of claim 1, wherein the solution has a shelf life greater than about three weeks.

6. A stable, sterilized, infusion solution comprising argatroban dissolved in a first solvent and a second solvent, the solution having an argatroban concentration ranging from about 15 mg/mL to about 250 mg/mL and a pH ranging from about 4.5 to about 6.5, wherein the first solvent is selected from the group consisting of propylene glycol, polyethylene glycol 100-1000, benzyl alcohol and combinations thereof and wherein the second solvent is different than the first solvent and is selected from the group consisting of propylene glycol, polyethylene glycol 100-1000, benzyl alcohol and combinations thereof.

7. The solution of claim 6 comprising an acid.

8. A stable, sterilized, infusion solution comprising argatroban dissolved in an acetic acid, the solution having an argatroban concentration ranging from about 15 mg/mL to about 250 mg/mL, a first solvent selected from the group consisting of propylene glycol, polyethylene glycol 100-1000, benzyl alcohol and combinations thereof, and a second solvent different than the first solvent, the second solvent selected from the group consisting of propylene glycol, polyethylene glycol 100-1000, benzyl alcohol and combinations thereof.

9. A stable, sterilized, infusion solution comprising argatroban dissolved in an acid, the solution having an argatroban concentration ranging from about 15 mg/mL to about 250 mg/mL and a pH ranging from 1.0 to about 3.5, a first solvent selected from the group consisting of propylene glycol, polyethylene glycol 100-1000, benzyl alcohol and combinations thereof, and a second solvent different than the first solvent, the second solvent selected from the group consisting of propylene glycol, polyethylene glycol 100-1000, benzyl alcohol and combinations thereof.

* * * * *